United States Patent [19]

Wakatake

[11] Patent Number: 4,834,944
[45] Date of Patent: May 30, 1989

[54] AUTOMATIC ANALYTICAL APPARATUS

[75] Inventor: Koichi Wakatake, Koganei, Japan

[73] Assignee: Mitsubishi Chemical Industries Limited, Tokyo, Japan

[21] Appl. No.: 40,719

[22] Filed: Apr. 20, 1987

Related U.S. Application Data

[63] Continuation of Ser. No. 547,220, Oct. 31, 1983, abandoned.

[30] Foreign Application Priority Data

Nov. 9, 1982 [JP] Japan ................................ 57-196584

[51] Int. Cl.$^4$ .......................................... G01N 35/04
[52] U.S. Cl. ...................................... 422/64; 422/67; 422/100
[58] Field of Search .................... 422/63–65, 422/67, 100; 364/397; 141/168, 169

[56] References Cited

U.S. PATENT DOCUMENTS 4,311,667 1/1982 Gocho .................................. 422/64

Primary Examiner—Michael S. Marcus
Attorney, Agent, or Firm—Oblon, Fisher, Spivak, McClelland & Maier

[57] ABSTRACT

An automatic analytical apparatus comprising a sample cassette for holding a plurality of cups each containing a sample, a pipette means for pipetting the sample contained in the cup into a reaction tube transferred to a predetermined position, a transport means for holding the reaction tube at predetermined spaces, a driving means for intermittently driving the transport means, a diluent pipetting means for pipetting a diluent into the reaction tube containing the sample at a predetermined position according to a measuring item, a pipette transfer means for measuring the sample and the diluent added thereto and for discharging them into a reaction tube held in a measuring turret, a reagent pipetting means for pipetting a reagent according to the measuring item into the sample and diluent in the reaction tube held in the measuring turret, a transfer means for transferring the reaction tube containing the sample, the diluent and the reagent to an absorptiometry position, and an optical measuring means for optically executing an absorptiometry of the sample by irradiating beam of a light source.

6 Claims, 7 Drawing Sheets 4,834,944

AUTOMATIC ANALYTICAL APPARATUS

This application is a continuation of application Ser. No. 547,220, filed on Oct. 31, 1983, now abandoned.

BACKGROUND OF THE INVENTION

1. Field of the Invention

This invention relates to an automatic analytical apparatus. More particularly, this invention relates to an automatic analytical apparatus for analyzing a collected blood sample immunologically.

2. Description of the prior art

In the field of immunological analysis of the blood sample it is absolutely essential to dilute the sample (serum) to a certain concentration and subsequently to stir the diluted sample and a reagent added thereto as soon as possible prior to the initiation of the reaction thereof so as to measure the process of the reaction such as agglutination reaction.

Hitherto there has not been developed an analytical apparatus for automatically conducting a series of these operations in this field since these operations are complicated. Especially, it might be an obstacle to develop the automatic apparatus that the analysis of this type requires a relatively high magnification of dilution of the sample. Illustratively stated, a large quantity of the diluent added thereto is required for a desired concentration of the sample and which requires a large volume container with the result of a large-size apparatus.

SUMMARY OF THE INVENTION

One of the primary objects of the present invention is to provide a novel automatic analytical apparatus comprising means for diluting a sample, measuring the diluted sample and pipetting a reagent to a desired amount of the sample.

The present invention resides in an analytical apparatus comprising a sample casette for holding a plurality of cups each containing a sample, a pipette means for pipetting the sample contained in the cup into a reaction tube transferred to a predetermined position, a transport means for holding the reaction tube at predetermined spaces, a driving means for intermittently driving the transport means, a diluent pipetting means for pipetting a diluent into the reaction tube containing the sample at a predetermined position according to a measuring item, a pipette transfer means for measuring the sample and the diluent added thereto and for discharging them into a reaction tube held in a measuring turret, a reagent pipetting means for pipetting a reagent according to the measuring item into the sample and diluent in the reaction tube held in the measuring turret, a transfer means for transferring the reaction tube containing the sample, the diluent and the reagent to an absorptiometry position, and an optical measuring means for optically executing an absorptiometry of the sample by irradiating beam of a light source.

DETAILED DESCRIPTION OF THE PREFERRED EMBODIMENTS

Figure 1:
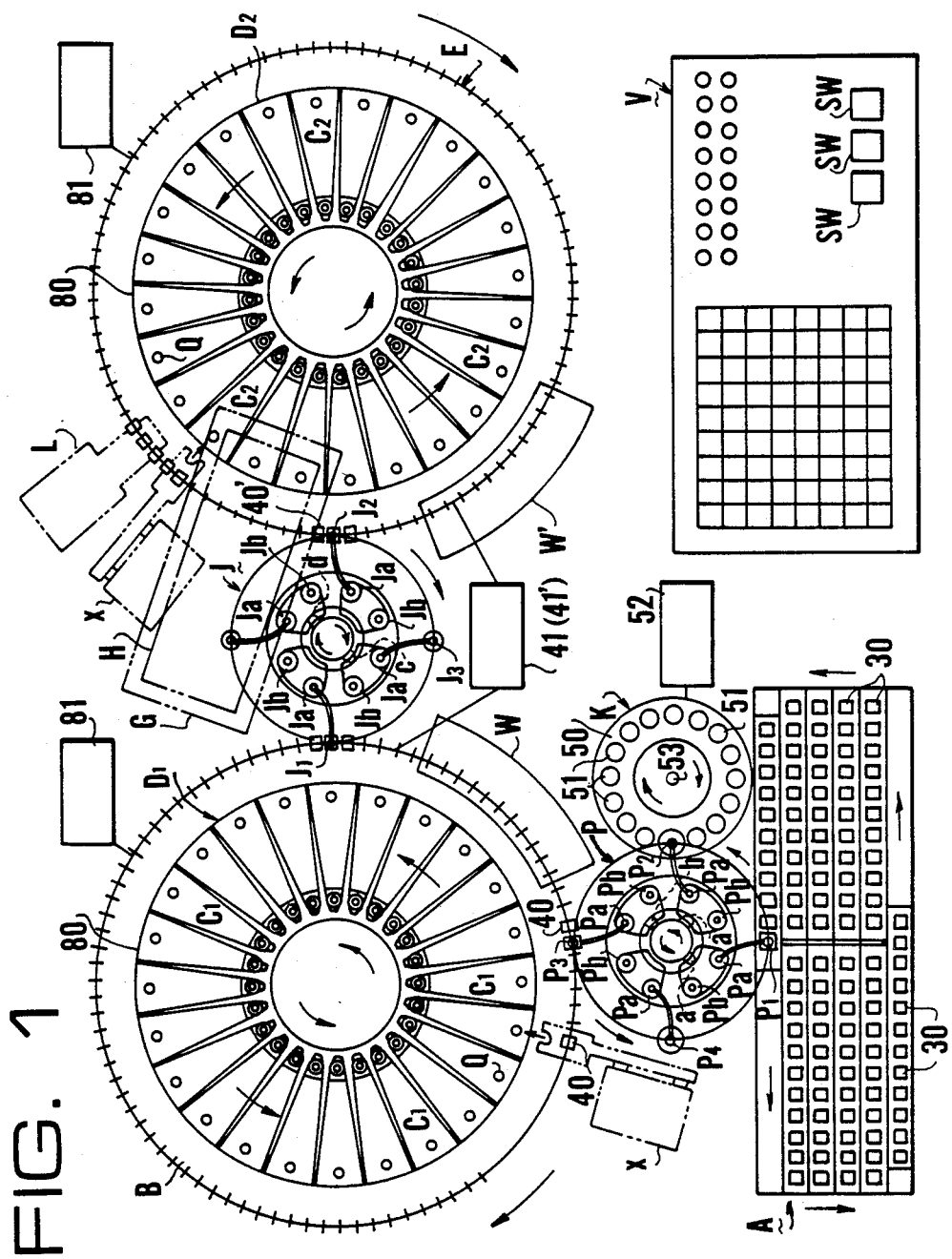
FIG. 1 is a schematic top plan view illustrating a preferred embodiment of an automatic analytical apparatus made in accordance with the present invention.

Referring now to the drawings, and in particular to FIG. 1, the present invention is illustrated, by way of example, as being embodied in an automatic analytical apparatus for immunological serum inspection, a plurality of sample cassettes A for ordinary samples holding a plurality of cups 30 each of which may contain a predetermined amount of serum for measuring (in the embodiment illustrated, one sample cassette contains 10 cups for ordinary samples and one cup for a control sample), a sampler K holding samples for emergency, a sample pipette device P sucking up the ordinary samples or the emergency samples in a predetermined amount at a predetermined position to inject into a reaction tube 40, a turret shaped transport means B holding a plurality of the reaction tubes 40, a diluent device D being disposed along the inner periphery of the turret transport means B in a coaxial relation with the transport means B and having a plurality of bottles C removably on a turret holder 80 which each contains a first diluent corresponding to measuring items, a pipette transfer device J transferring the reaction tubes 40 containing a predetermined amount of ordinary or urgent samples diluted with a predetermined amount of the first diluent of predetermined type to a predetermined concentration from the transport means B to a reaction tube 40' held by a measuring turret table E, an optical device G measuring absorptiometry of the sample contained in the reaction tube 40', a digital processor H indicating and memorizing data determined by the optical device G and cleaning devices W and W' respectively cleaning the reaction tubes 40 and 40' after the above-described first diluting operation and measuring operation were finished.

Figure 2:
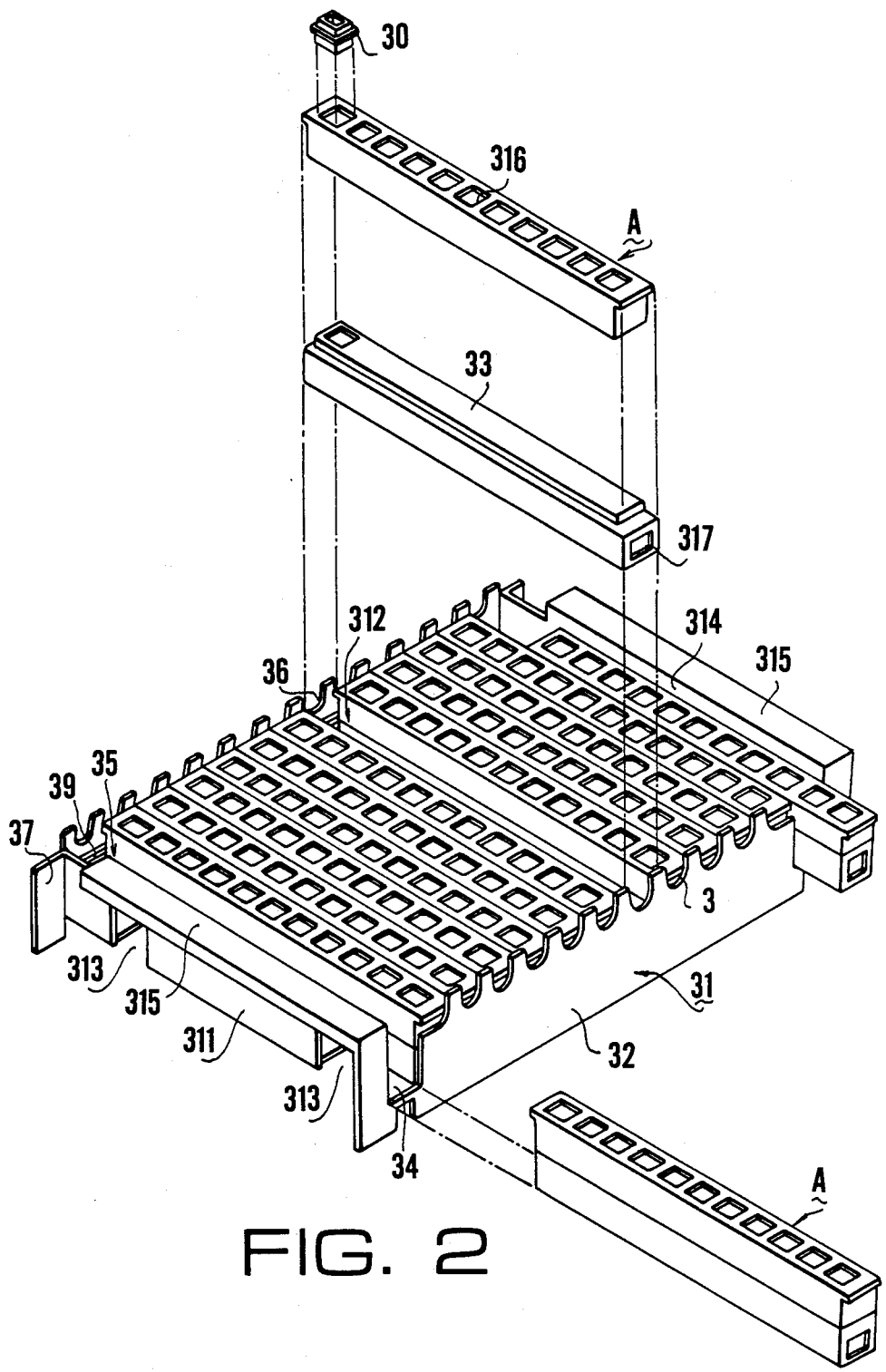
FIG. 2 is a perspective, partial, combined fragmentary view illustrating a preferred embodiment of a sample cassette and a cassette tray made in accordance with the present invention.

A plurality of the above sample cassettes A for ordinary samples are held in parallel relation in a cassette tray 31 as illustrated in FIG. 2.

This cassette tray 31 is formed in the shape of a rectangular box and at the front and back ends of right side wall 32 has a cut out portion (notch) 34, 35 formed in a shape of rectangle so as to introduce the sample cassette A for an ordinary sample mounted on a stand 33 as illustrated in FIG. 2. In addition, there are provided in the cassette tray at the top edge portions of the right and left side walls 32 and 37, a plurality of cut out portions 36 each having generally the shape of a half circle corresponding to the width of the sample cassette A and provided at the inner surfaces of the right and left side walls 32 and 37 along the lower portions of the half circle-cut out portions 36, guide portions 39 for sliding the sample cassette A along a longitudinal direction of the walls 32 and 37. Near an abutting portion of a front wall 311 and a bottom wall 312 are provided generally rectangular two holes 313 through which arms of a longitudinal transfer means IV (shown in FIG. 4) of the sample cassette A move back and forth. At upper portions of the front wall 311 and rear wall 314 are provided grip portions 315 for carrying out the cassette tray 31. The cassette tray 31 is removably fitted in a sampler. In FIG. 2, the sample cassette A is formed in a generally rectangular parallelepiped configuration and has the same length as the width of the cassette tray 31.

Further, at an upper surface of the sample cassette A, there are provided eleven (11) rectangular holes 316 in which the above described cups 30 are removably fitted. A number 33 is a stand which removably fits in a lower end portion of the sample cassette A and has the same length as the sample cassette. An upper portion of the stand 33 is of two stage structure so as to fit in the sample cassette A at the stage thereof.

In addition, at the upper end portion of the stand 33 there is provided a light transmitting hole for reading a code and at the bottom portion of the stand is to be provided a hook hole 317 according to the cut out portion of the hole 316 of the sample cassette A. This hook hole 317 is used as a stopper when the sample cassette A is cross-transferred.

Thus, when the ordinary sample cassettes A are to be arranged in the cassette tray 31, at first samples (serum) to be measured are charged to each cup 30, and each cup 30 is set in the sample cassette A. Next, the sample cassettes A are put in the stands 33 to build up two stage structure, then are sequentially disposed in order in the cassette tray 31 to fill the interior of the cassette tray 31 with the sample cassettes A.

The cassette tray 31, so prepared with the sample cassettes A, are set on the sampler at a predetermined position.

When the analytical apparatus is switched on, the sample cassette A in the front line of the cassette tray is first moved from the cut out portion 35 to the crossed arrow direction (shown in FIG. 1) intermittently together with the stand 33 by a sample cassette cross transfer means IH (shown in FIG. 3) so that each of the cups 30 successively reach a position P$_1$ where a sample is sucked up according to necessity. This cross-movement of the sample cassette A in the front line of the tray is transmitted to a sample cassette disposed adjacent to the cassette A to push the adjacent sample cassette transversly at the same speed. When the sample cassette in the front line reaches the adjacent tray, a longitudinal transfer means IV (shown in FIG. 4) of the sample cassette is put into operation and extends a sending-out arm through the holes 313 to push the stand 33 in the last line of the cassette tray in a forward motion. At this time, all of the sample cassette A for ordinary samples in the cassette tray 31 slide forwardly with the stand 33 by the space of side width of one cassette. When the last sample cassette in the tray advances, the cross-transfer means IH is again put into operation and the same action as the above is repeated, whereby new sample cassettes are successively transferred to the cassette tray 31 through the cut out portion 34.

Figure 3:
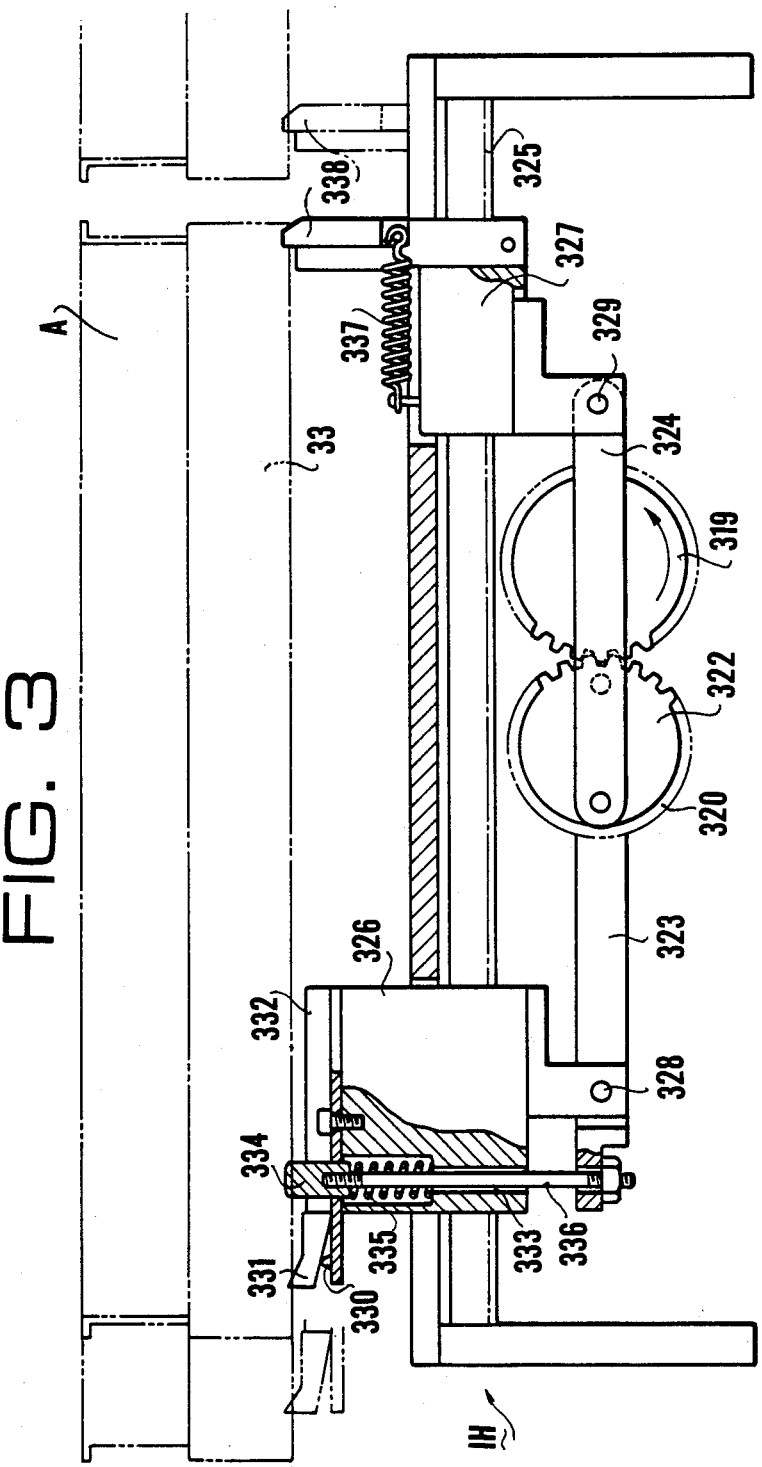
FIG. 3 is a vertical sectional view illustrating a cross-transfer mechanism of the sample casette shown in FIG. 2.

Referring to FIG. 3, in the cross-transfer device IH comprising a part of a sample cassette transfer means, a power from a motor is first transmitted to a gear 319 and next, to a gear 320. In the gear 320, a driving ring 322 is provided so as to interlock to the gear 320 and one end each of the links 323 and 324 are mounted on the gear 320 and the driving ring 322 in a diagonal line with respect to a supporting pillar. The other end of the link 323 mounted on the gear 320 is pivotably connected to a pin 328 at a lower portion of a first slider 326 which is slidably mounted on two parallel horizontal axes 325, and the link 324 mounted on the driving ring 322 is pivotably connected to a pin 329 at a lower portion of a second slider 327 which is slidably mounted on horizontal axes 325 as described above. Both the first and second sliders are supported by the horizontal axis 325 extending into throughholes made in center portions of the bodies thereof.

On a tip end of the first slider 326 is mounted a claw 331 which is urged by a compression coil spring 330. The claw 331 has an upwardly tilting configuration. A number 332 is a claw holder. Further, the first slider 326 has a throughhole 333 which perpendicularly penetrates into the first slider, at a backward position of the claw 331. The shaft 336 penetrating into the throughhole 333 has at an upper portion thereof a chip 334 urged by compression coil springs 335 and is connected to a tip end of the link 323 at a lower portion thereof.

The second slider 327 has at a tip end thereof a claw 338 which is urged by tension spring 337 and has an upper surface inclined upwardly to the same direction as that of the claw 331.

The claws 331 and 338 of the cross-transfer device IH, so formed, engage the hole 317 formed in the bottom of the stand 33 to enable the cross-transfer of the sample cassette A.

When the signal from the control device (CPV) is output to the cross-transfer device, a motor is driven to make the gears 319 and 320 full one revolution to the arrow direction as illustrated in FIG. 3. While the gears 319 and 320 rotate 180°, the links 323 and 324 move to the opposite directions from each other and with this movement, two sliders 326 and 327 also slide to the opposite directions from each other. In this case, the claw 331 engage the hole 317 formed in the bottom of the stand 33 to allow the stand 33 to slide to a cross direction by the distance of one cup. When the slider 326 returns, the claw 331 is pushed downwardly by virtue of the weight of the stand 33 and the sample cassette A. When the gear 320 makes one revolution, the claw 331 fits in the next hole of the stand 33. The chip 334 projects into the hole 317 while the slider 326 moves forwardly, but when the slider 326 returns, the chip returns in a downwardly pulled state rather than the normal state since a tip end of the link 323 connected to the shaft 336 descends through a pin 328 as a supporting point.

A claw 338 fixed in the second slider 327 falls in an arrow direction as shown in FIG. 3 by virtue of the operation of a tension spring 337 while the slider 327 slides backwardly. When the slider 327 reaches backwardly at the maximum, the claw 338 engages the hole 317 of the next stand 33 in the first line of the cassette tray and when the slider 327 returns, it allows the stand 33 to slidably move one step.

This return motion of the slider 327 is transmitted to the slider 326. Thus, the claw 331 of the first slider 326 and the claw 338 of the second slider 327 each moves independently the stand 33 and accordingly, stepwise delivers the sample cassette A integral with the stand 33 to the cross direction.

Figure 4:
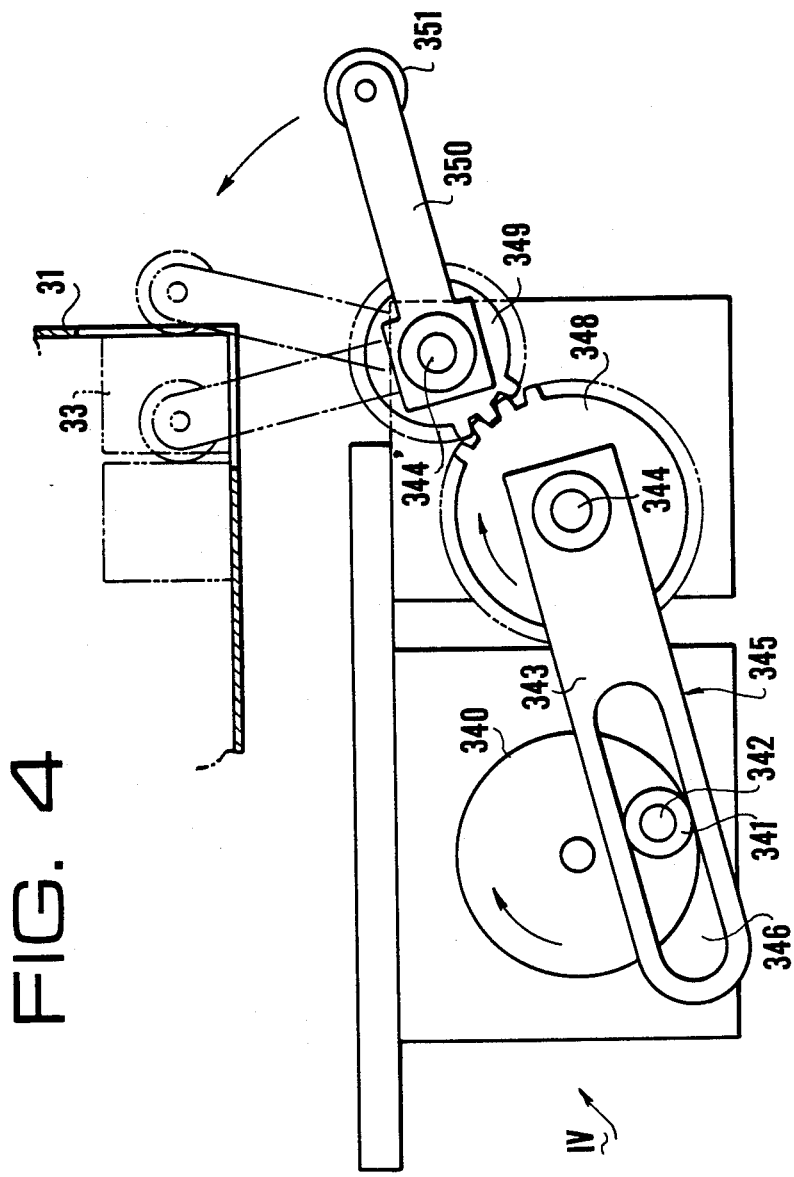
FIG. 4 is a vertical sectional view illustrating a longitudinal transfer mechanism of the sample cassette shown in FIG. 2.

At the time when this cross movement is terminated, a signal to the longitudinal transfer device IV as shown in FIG. 4 is input. Referring to FIG. 4, in the longitudinal transfer device IV, power from a motor provides a rotational motion to a crank 340. At one end of the periphery of the crank 340, a ball bearing 341 is provided through a bearing pin 342. This ball bearing 341 slides along an inner periphery of an elongated slot 346 which is provided at a tip end of a rocker arm 345. The rocker arm 345 has a base end 343 fixed to a shaft 344 and a bearing shaft. The opposite ends of the shaft 344 rotate depending on a rotation of the bearing 347 and conjointly with the up and down movement of the rocker arm 345. A flat gear 348 having a large diameter is fixed to this shaft 344 and intermeshes with a flat gear 349 having a small diameter which is fixed to the shaft 344′ provided in parallel to the shaft 344. The shaft 344′ has two delivery arms 350 fixed thereto at a suitably adjusted angle, and rotates depending on a rotation of a bearing. The roller 351 of the tip end of arm 350 is rotatable and relieves the contact resistance at the time of the delivery of the stand 33 disposed in the last line of the cassette tray 31. Therefore, when a longitudinal transfer signal is input to the computer provided, a motor is driven to make the crank 340 full one revolution to an arrow direction. With this rotation, the ball bearing 341 rotates on the crank 340 sliding along the elongated slot 346 provided in the rocker arm 345, whereby the rocker arm 345 rocks with the bearing pin as a center supporting axis 344 in upward and downward directions. As the ball bearing 341 moves upwardly, the flat gear 348 rotates to an arrow direction illustrated in FIG. 4, and the delivery arm 350 swivels upwardly depending on the rotation of the flat gear 349 having a relatively small diameter. In the swiveling process, the roller 351 provided at the tip end of the delivery arm 350 abutts engagement with the rear side surface of the last stand 33 in the cassette tray 31 and in successive swiveling, allows the stand 33 to slide forward. The delivery arm 350 pushes the stand 33 continuously until the tip end of the rocker arm 345 reaches the uppermost position. The flat gears 348 and 349 rotate in opposite directions from each other meshing with the movement of the rocker arm 345, whereby the delivery arm 350 downwardly swivels and returns to the original position. The distance in which the stand 33 slidably advances by one swivel of the delivery arm 350 is predetermined to be one step. At the time the operation of longitudinal delivery is finished, a signal is transmitted to the cross-transfer means and similar operation as described before is repeated.

Thus, each of the sample cassettes A mounted on the stands 33 is moved to a cross direction and to a longitudinal direction by the transfer devices which are driven by the signal input at predetermined intervals, and the sample (serum) is injected into each of the reaction tubes 40 by a pipette device P in a predetermined sucking position $P_1$.

In the drawings of FIGS. 1 and 2 illustrated as one embodiment of the present invention, the sample cassette A contains 11 cups of samples at one time and the samples are contained in cups 30 each having the same configuration. 10 cups of the samples counting from the right hand contain human serum as the ordinary samples and the last one cup contains quality control sample such as serum of animal, artificial serum or the like.

Thus, it is preferred that the measurement is made in a combination of 10 ordinary samples and one quality control sample. However, it is not necessary to prepare such a quality control sample in every specimen sample cassette. It may be arranged in every other line or every five lines of the sample cassettes. In order to obtain a more precise measured value, it is preferred that each sample cassette A contain the quality control sample.

Both of the ordinary samples and the control sample measured in the same conditions, that is, being sucked by the pipette device P in the sucking position, injected into the reaction tubes 40 and optically measured by the optical device G. In addition, a signal treating device H receives the signal of transmittance corresponding to each reaction tube 40 and computes to give the result automatically. The measured result of the ordinary sample is treated by consecutive numbers different from that of quality control sample. Thus, since the number of the ordinary sample is a multiple of number 10, the relationship of the data and the sample can be easily understood. The measured result of the quality control sample is compared with a standard value of the control sample in the digital processor H to automatically detect the deviation at the measuring time in the analysis apparatus, whereby the next measured value of 10 samples of the ordinary samples are modified. Thus, the value resulted in the periodical measurement of the control sample correct the measured value of the ordinary sample before the next control sample is measured.

Further, the reliability of the measured value in the overall measurement may be cleared from the degree of scattering of the measured value of the control samples during the measuring time compared with a standard value of the control sample after the measurement of the samples in the sample cassette A.

In addition, in the present invention it is not necessary to prepare the control sample in every sample cassette A as before described. If an empty cup, without containing the control sample is set in the sample cassette, the position thereof is memorized previously in the digital processor H and quickly fed by a skip means (not shown in the Figure) when the empty cup is transferred to the sample sucking position, whereby a cup containing an ordinary sample is quickly transferred to the sucking position saving time. The skip means is so constructed that the sample cassette cross-transfer means IH works two times continuously and moves the ordinary sample cassette continuously in two steps.

The sampler K is provided for urgent samples, and removably abuts against the pipette device P as illustrated in FIG. 1.

A sample necessitating emergency analysis, for example, for data about an emergency operation, is contained in a plurality of vessels 51 which are held in a turret plate 50. The turret plate 50 is rotated intermittently around a shaft 53 by a driving means 52. When the vessel 51 is transferred to a position $P_2$ of sucking the urgent sample in the pipette means P, the pipette means P actuates to suck up a predetermined amount of the sample. The operation in this case is controlled by the digital processor H so that the driving operation of the sample cassette A for the ordinary samples is immediately stopped. After all of the urgent samples are analyzed, the driving means of the ordinary sample automatically starts to work. To facilitate the analysis of the urgent sample, as shown in FIG. 1 it is enough to exchange the switch in the operation panel V from a switch $SW_1$ for ordinary samples to a switch $SW_3$ for urgent sample. $SW_2$ as shown in FIG. 1 is a stop switch.

The pipette means P comprises 4 pipettes held in a turret pipette holder in a predetermined spaces shown in FIG. 1 and is controlled so as to intermittently move to a counterclockwise direction by a 90° arc by a motor (not shown in the Figure) and a conventional cam mechanism or the like.

Each of the above-mentioned pipettes sucks an ordinary sample at the $P_1$ position unless an urgent sample is to be sucked. In the latter case, the pipette does not function at the $P_1$ position but instead sucks the urgent sample at the $P_2$ position. In either case, the sucked liquid is discharged together with the buffer solution into a reaction tube 40 at the $P_3$ position. Then the pipette holder moves to position $P_4$ to clean up the pipettes and sequentially returns to position $P_1$ again.

In addition, each of the pipettes is fitted with a pump P consisting of a sucking pump Pa and a discharge pump Pb as shown in FIG. 1, which pumps Pa and Pb engage cams for sucking and discharging the samples at a predetermined position. And the motion of the cams are controlled by the digital processor H.

When the ordinary samples are sucked and discharged, the sucking pump Pa and the cam a for each of the pipettes engage each other at the position $P_1$ as shown by a solid line in FIG. 1, and the discharge pump Pb and the discharge cam b for each of the pipettes engage each other at the position $P_3$. When the urgent samples are sucked and discharged, the cam a for sucking the samples moves so as to engage the sucking pump Pa at the position $P_2$ and the cam b is arranged to engage the discharge pump Pb at the position $P_3$. When the sucking and discharging of the urgent samples are finished, the sucking cam a returns automatically to the sucking position $P_1$ for the ordinary samples from the position $P_2$ according to an instruction signal from the digital processor H.

Thus, the reaction tubes 40 filled with the ordinary or urgent samples are held in the transport means B (in the shape of a turret) which is intermittently rotated by the driving means 41 such as Geneva gear and transferred to a position for charging a diluent, where a first diluent is charged to the reaction tubes 40 by a first diluent means $D_1$ according to a measurement item.

Figure 5:
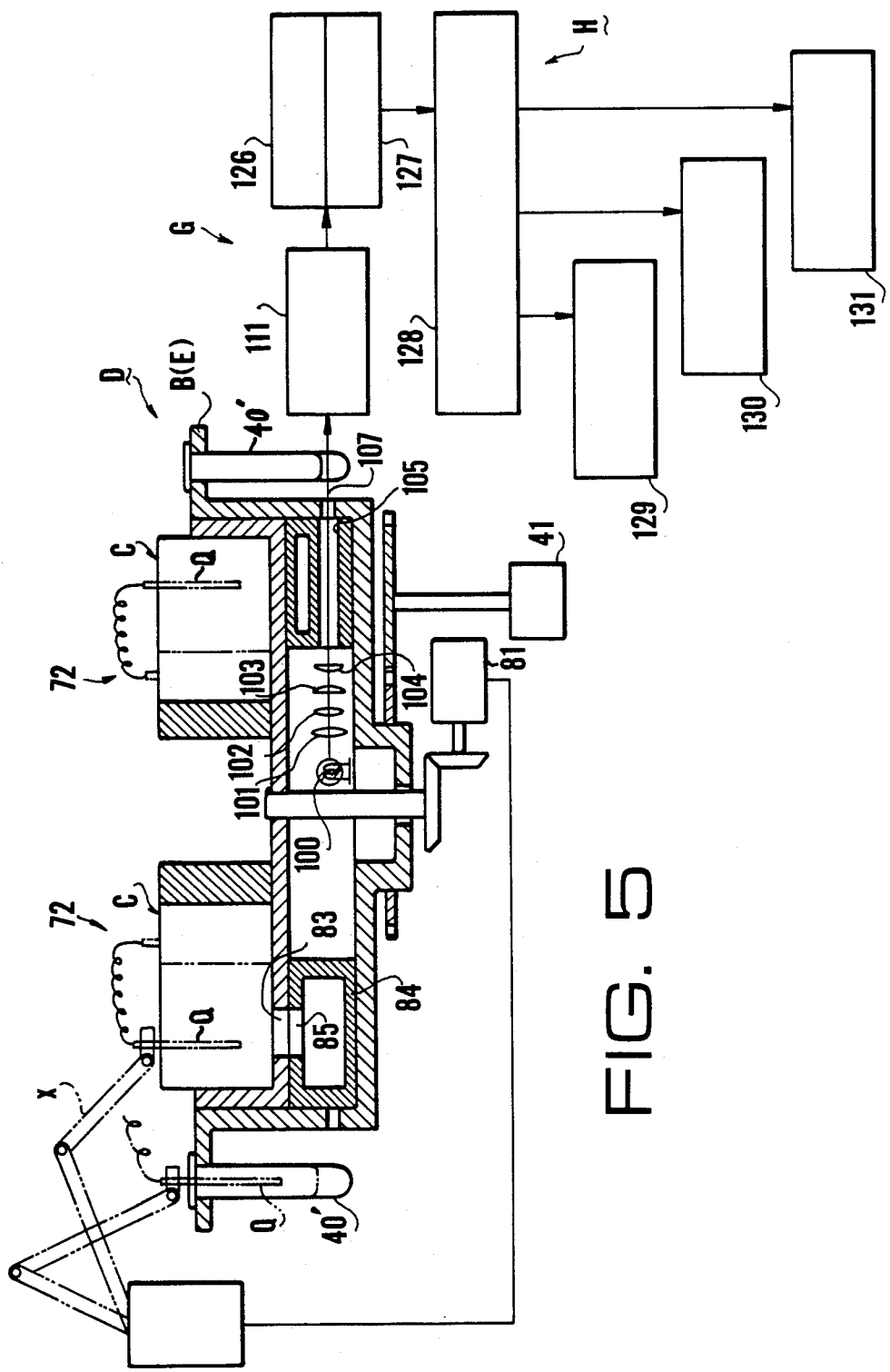
FIG. 5 is a vertical sectional view illustrating a combined structure of a feeder and a diluent device or a reagent device in combination with an optical device and a digital processor.
Figure 6:
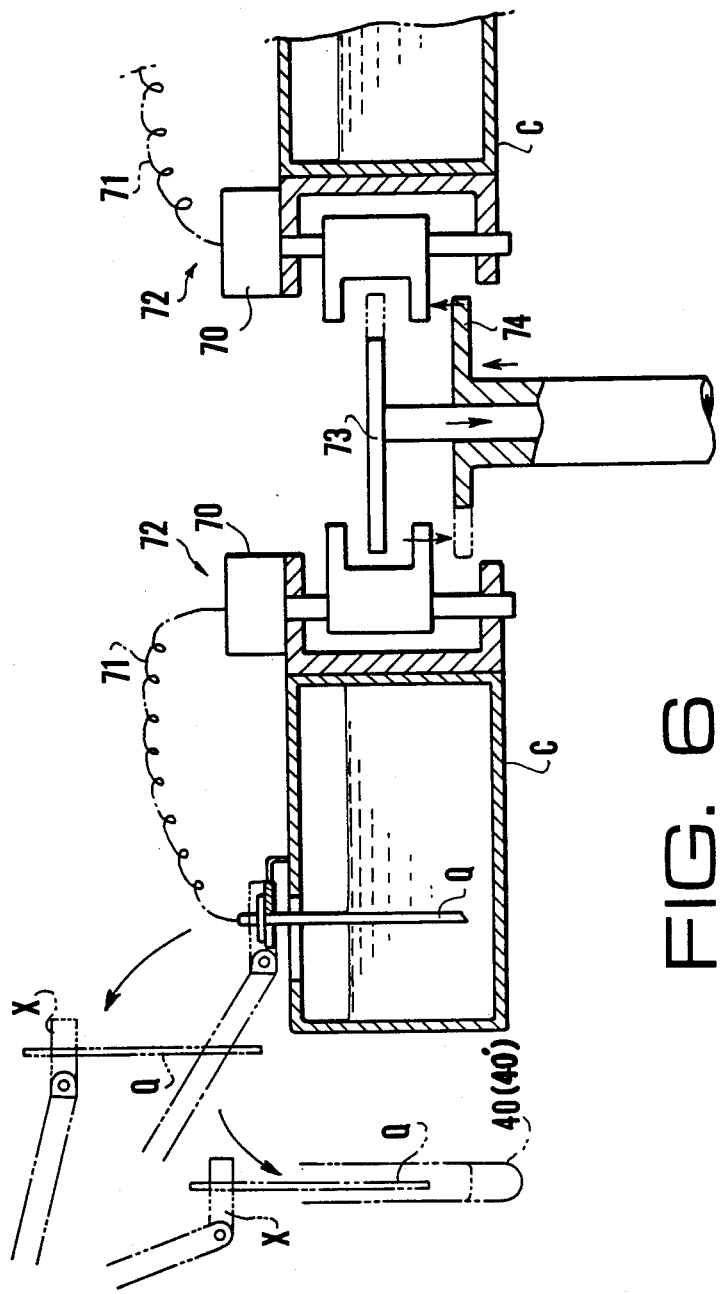
FIG. 6 is an enlarged vertical sectional view illustrating the diluent device or reagent device shown in FIG. 5.

Referring to FIGS. 5 and 6, the first diluent means $D_1$ and a reagent device $D_2$ each comprises a bottle C being made of a light-transmitting material at least at the bottom thereof, and being mounted on a holder 80 having a shape of a turret made of a light-transmitting material; a driving means 81 transferring the bottle C to the charging position at a high speed; and a pipette Q measuring up a liquid or a reagent from the bottle C and discharging it into the reaction tube 40 or 40'. Particularly, the turret holder 80 is disposed in the interior of the transport means B in coaxial relation and on the turret holder 80, a plurality of the bottles C are radially and removably mounted and in the bottle C various diluents or the reagents are contained according to the analysis items. Thus, the turret holder 80 is controlled by the driving means 81 so as to rotatably transport the diluents or the reagents necessary for analysis.

Under the turret holder 80, a duct 84 made of a light-transmitting material is provided in coaxial relation with the turret holder 80. On an upper surface of the duct 84, a cool air supplying hole communicating with the throughhole 83 is provided at predetermined spaces to preserve the diluent or the reagent in cooling, if necessary. The duct 84 is fixedly provided and does not rotate with the turret holder 80.

When the reagent bottle C containing the first diluent according to the measuring items is transferred at a high speed to the position where the diluent is charged in the manner as described herein, the expansible pipette Q mounted on each reagent bottle C is pulled out and led to the position of the reaction tube 40 by a holding means X and thereby to charge the first diluent to the reaction tube 40 in a predetermined amount.

More particularly, at the backward position of the bottle C, there are provided, as illustrated in FIG. 6, a liquid measuring and discharging means 72 comprising a pump 70, a pipette tube 71 being connected to and expansibly held by the pump 70 and the pipette Q being connected to the end of the pipette tube 71. The pump 70 engages a projecting portion of a cam 73 rotating clockwise and counterclockwise and descends to suck up the first diluent. Then, the cam 73 releases the engagement with the pump 70 and returns to the neutral position. Thereafter, the arm of the holding means X extends to hold the pipette Q, pulls the pipette Q inserted in the bottle C outwardly from the bottle C, leads it to the reaction tube 40, whereby the first diluent is charged to the reaction tube 40 by the pipette Q in a predetermined amount with the ascension of a second cam 74. At this time, the pipette tube 71 is led to a predetermined position since it is expansible. Thereafter, the holding means X releases the holding of the pipette Q while the pipette Q returns to the original position by means of a spring or the like. Thereafter, the pump 70 again engages the cam 73 and the same operation as explained above is repeated to make the pipette Q suck up a predetermined amount of the first diluent.

Thus, the reaction tube 40 containing the sample and the first diluent is intermittently transferred to a predetermined position. The diluted sample, so transferred to the predetermined position, is further measured and discharged into the reaction tube 40' held in the measuring turret E by the pipette transfer means J.

This pipette transfer means J comprises a structure similar to that of the pipette means P and includes 4 pipettes held by the turret pipette holder at predetermined intervals as shown in FIG. 1 and intermittently moves to the clockwise direction by 90° under the control of a motor (not shown in the FIG.) and known cam mechanisms. Each of the pipettes sucks a predetermined amount of the sample diluted with the first diluent at position $J_1$, then intermittently moves twice and discharges the sample into the reaction tube 40' held in the measuring turret E. At this time when the sucked sample is discharged into the reaction tube 40', a buffer liquid as a second diluent, or distilled water, is charged to the reaction tube 40' by a buffer liquid supplying means (not shown in the Figure). If the measuring items do not require the second dilution, the signal for processing the second diluent charging operation is automatically cancelled. Thereafter, the pipette holder is intermittently transferred to position $J_3$ for cleaning the pipettes and sequentially again transferred to the position $J_1$. Each of the pipettes is provided with the pump P comprising a sucking pump Ja and discharging pump Jb which respectively engage a sucking cam c and a discharging cam d at a predetermined position under the control of the digital processor H to work.

Illustratively stated, when the pipette sucks the sample, the sucking pump Ja engages the cam c at position $J_1$ and when the pipette discharges the sample, the discharging pump Jb engages the cam d at position $J_2$. Conjointly with the discharging operation of the discharging pump Jb, the buffer supplying means is actuated to supply the second diluent to the reaction tube 40'.

The diluted sample in the reaction tube 40' is transferred to the position for charging the reagent in the measuring turret E transmittently rotating simultaneously with the transfer means B.

The structures and operations of the reagent device $D_2$, the pipette Q and the holding means X which are disposed in the measuring turret E are the same as those of the first diluent device $D_1$, so duplicate explanation is omitted here by applying the same symbols.

The reaction tube 40', thus charged with the second diluent, is transferred to a stirring position. The stirring is sequentially made by a conventional supersonic vibration means L in such a manner as not disturbing the rotation of the measuring turret E, i.e., holding up the reaction tubes simultaneously with the operation of the pipette transfer means J.

The optical device G disposed in the measuring turret E comprises a light beam from a light source lamp 100 converged by lenses 101, 102, 103 and 104 for advancing in a cylindrical portion 105, transmitting through the reaction tube 40' from a hole 107 provided on the measuring turret E, and being detected by a sensor element 111.

More specifically, the hole 107 is formed in a vertical wall portion of the measuring turret E and in an orthogonal direction to the reaction tube holding axis, and in the position where the light beam can be transmitted through the object for the measurement (in the reaction tube 40').

Simultaneously with the rotation of the pipette transfer means, the measuring turret E rotates at least 360°, preferably 360° plus one pitch, in the state of holding the reaction tube 40' during one intermittent motion of the pipette transfer means so that the measurement by the optical measuring device is applied several times or many times to one reaction tube 40' held by the measuring turret E, whereby precision of the measurement is improved and the change of transmittance of each reaction tube 40 during the reaction can be easily measured.

Thus, the data obtained in the absorptiometry are transmitted to the digital processor H as illustrated in FIG. 5 The digital processor H comprises a logarithmic converter 126, an A/D converter 127 converting the analysis data which are input to the logarithmic converter 126 to a digital signal, an interface 128, a microcomputer 129 for memorizing the signal. After the optical measurement was made in plural times according to the measuring items, the obtained data are compared with each other to be calculated by the computor, whereby the concentration value of the analytical items is displayed with a printer 130. A CRT 131 indicates the analyzed data or the statistical data.

The reaction tubes 40 and 40', after measurement, are transferred to cleaning means W and W' to be washed.

Figure 7:
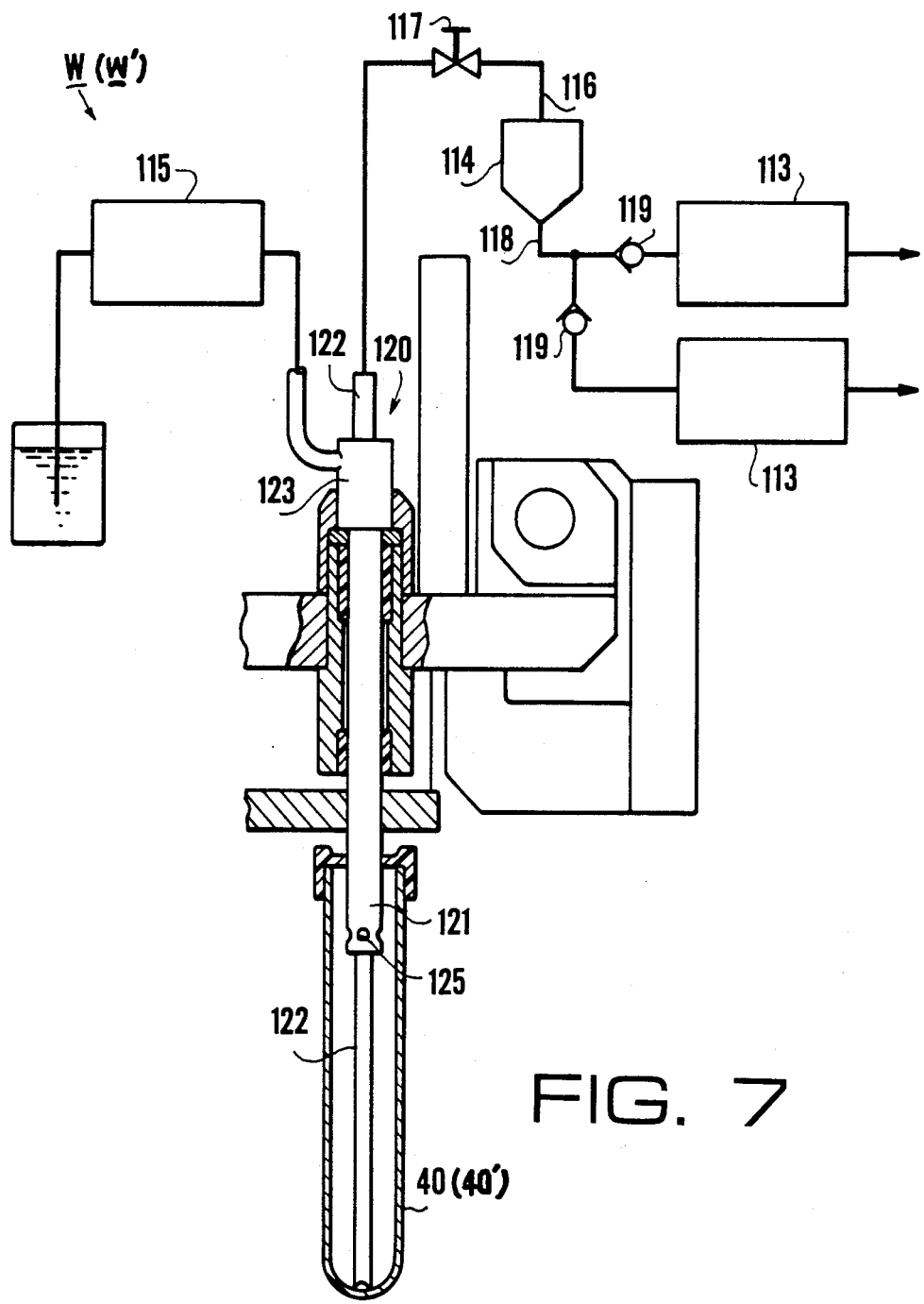
FIG. 7 is a vertical sectional view illustrating a cleaning device made in accordance with the present invention.

The cleaning means W and W' have the same composition and are comprised, as illustrated in FIG. 7, of two vacuum pumps 113 sucking and discharging cleaning water, a vacuum tank 114 being connected to the vacuum pumps 113, a cleaning nozzle 120 being connected to the vacuum tank 114 and dropping downwardly to the reaction tube 40 (40') at the time of cleaning, a water supply pump 115 hydraulicly supplying cleaning water to the cleaning nozzle 120, an electromagnetic valve 117 disposed in a water pipe 116 being connected to a drain side of the cleaning nozzle 120 and the vacuum tank 114, and check valves 119 disposed in water pipes 118 being connected to the vacuum pumps 113 and the vacuum tank 114.

The cleaning nozzle 120 is comprised of a cleaning water charging pipe 121 having a large diameter and a short length, and a cleaning water discharging pipe 122 disposed in the cleaning water charging pipe 121 and having a narrow diameter and long length. The cleaning water discharging pipe 122 is held by a seal material disposed in the opposite end portions of the cleaning water charging pipe 121, in coaxial relation with the cleaning water charging pipe 121. Further in the cleaning water charging pipe 121 at the lower end, a plurality of holes 125 are disposed radially in order to dispense cleaning water toward the inner wall of the reaction tube 40 (40'). The seal placed on the top end of the cleaning water charging pipe 121 has a connecting nozzle which dispenses cleaning water from the water pump 115 to a passage defined by the inner wall of the cleaning water charging pipe 121 and the outer wall of the cleaning water discharging pipe 122.

Thus comprised cleaning means W and W' function as follow:

First, when the reaction tube 40 containing the sample diluted with the first diluent and measured by the pipette transfer means J and the reaction tube 40' already optically measured are transferred to respective positions just under the cleaning devices W and W', the respective cleaning nozzles 120 are lowered by respective lifting means (not shown in the Figure) and set to start the cleaning.

Then, cleaning water is hydraulicly dispensed into the cleaning water charging pipe 121 by the pump 115, then is radially sprayed toward the inner periphery wall of the reaction tube 40 (and 40') through the holes 125 and flows downwardly to the inner bottom portion of the reaction tube 40 (and 40') as cleaning out the reactant adhered on the inner periphery wall or suspended matter in air. Simultaneously with the watering operation of cleaning water, the vacuum pump 113 for discharging water starts to work so that cleaning water is instantaneously absorbed in the cleaning water discharging pipe 122 with the residue of the reactant or the like, hydraulicly transferred into the vacuum tank 114 and discharged. The cleaning operation may be repeated several times. After the cleaning treatment is finished, the reaction tube 40 (and 40') is transferred to the position to be used again.

It is possible to incorporate an ultrasonic cleaning treatment step in the multiple stage cleaning treatment course by the cleaning nozzle 120 to clean the reaction tube more completely.

A feature of the analytical apparatus in accordance with the present invention lies in the provision of means for automatically conducting a series of operations such as pipetting a sample into a reaction tube, diluting the sample to a desired concentration, pipetting a reagent to the sample and measuring the sample and further cleaning the reaction tube, and thereby achieving streamlined analysis operation and enhanced precision of the result.

Another feature of the analytical apparatus in accordance with the present invention lies in the provision of a pipette means for measuring the diluted sample and pipetting only a desired amount, of the sample into the reaction tube, thereby enabling the apparatus to be small-sized.

In accordance with the present invention, a measuring turret makes not less than one revolution for every one intermittent movement of the pipette transfer means and therefore the measurement for one sample can be made continuously(many times, whereby timely changes in the sample can be easily measured and reliability of measurement precision largely improved.

Further, in accordance with the present invention, different pipettes are used for the diluent and the reagent, and therefore the sample is free from contamination by foreign diluent and reagent and in addition, measurement ability can be increased about 5–10 times that of conventional apparatuses.

The automatic analytical apparatus of the present invention can be preferably used in the immunological analysis.

Having now fully described the invention, it will be apparent to one of ordinary skill in the art that many changes and modifications can be made thereto without departing from the spirit of the invention as set forth herein.

What is claimed as new and intended to be covered by Letters Patent is:

1. An automatic analytical apparatus comprising:
   a plurality of cups for containing samples to be analyzed;
   a sample cassette for holding said plurality of cups;
   a transport turret rotatable about a first axis and having disposed thereon a first plurality of reaction tubes;
   means for moving said transport turret to move said first plurality of reaction tubes to any of a number of discrete stations along a closed path;
   diluent pipetting means operatively associated with said transport turret for pipetting measured amounts of diluent into said first reaction tubes containing said samples;
   a measuring turret rotatable about a second axis and having a second plurality of reaction tubes disposed substantially at a circumference thereof;
   means for moving said measuring turret to move said second plurality of reaction tubes to any of a number of discrete stations along a closed path;
   a reagent turret coaxial with said measuring turret, being rotatable with respect to said measuring turret about said second axis;
   a plurality of reagent containers mounted on said reagent turret;
   a plurality of reagent pipetting means, each being mounted on said reagent turret at a position associated with one of said plurality of reagent containers for movement therewith;
   means for using each said pipetting means for pipetting measured amounts of reagent from only said one of said reagent containers and into one of said second reaction tubes containing said samples and diluent, whereby each of said pipetting means is dedicated to one of said reagent containers;
   means for moving said reagent turret with respect to said measuring turret so as to selectively position any desired one of said reagent containers and the associated reagent pipetting means at a desired one of said discrete stations;
   first pipette sample transfer means for pipetting samples contained in said cups into first reaction tubes;
   second pipette sample transfer means disposed between said measuring and transport turrets for taking up measured amounts of said sample and diluent from said first reaction tubes and for discharging said measured amounts into said second reaction tubes, said second pipette sample transfer means comprising a pipette holder turret rotatable through predetermined indexing angles, a plurality of pipettes disposed on said pipette holder turret, driving means for intermittently indexing said pipette holder turret, and pumping means for effecting said taking up and discharging of said measured amounts of sample and diluent;
   optical measuring means operatively associated with said measuring turret for making an absorptiometry measurement of said samples, diluent and reagent while contained in said second reaction tubes, by use of a light beam, at a given one of said stations of said measuring turret; and
   control means for respectively operating during sequential time intervals said first and second pipette sample transfer means, said means for moving said transport turret, said means for moving said measuring turret, and said means for moving said reagent turret, said control means maintaining the dedicated use of said pipettes and being effective during a time interval to cause, substantially simultaneously;
   said motion of said transport turret, said indexing of said second pipette sample transfer means, said rotation of said measuring turret, and said motion of said reagent turret to bring any of said reagent containers to any desired station of said measuring turret.

2. An automatic analytical apparatus as claimed in claim 1, wherein said second pipette sample transfer means further comprises means for selectively adding additional diluent to the withdrawn sample and diluent and for depositing said sample, diluent and additional diluent into said second reaction tubes in a measured amount.

3. An automatic analytical apparatus as claimed in claim 1, further comprising:
   a diluent turret coaxial with said transport turret, being rotatable with respect to said transport turret about said first axis, comprising a plurality of diluent containers and said diluent pipetting means, said diluent pipetting means comprising plural pipettes respectively mounted adjacent individual ones of said plurality of diluent containers; and
   means for moving said diluent turret with respect to said transport turret to selectively position any desired one of said diluent containers and the associated diluent pipette at any desired one of said discrete stations of said transport turret, wherein said control means is effective during said time interval to move said desired diluent container to said desired station.

4. An automatic analytical apparatus as claimed in claim 1, wherein said means for moving said measuring turret comprises means effective to move said measuring turret through a series of rotations, each rotation moving said second reaction tubes from one discrete station to another during said time interval and covering an arc greater than 360 degrees.

5. An automatic analytical apparatus as claimed in any of claims 1, 2, 3, or 4 wherein:
   said second pipette sample transfer means comprises at least three pipettes; and
   said apparatus further comprises pipette cleaning means disposed between said measuring and transport turrets for cleaning said pipettes of said second pipette sample transfer means, driving means for indexing said pipette holder turret of said second pipette sample transfer means to move said pipettes disposed thereon to a position for taking up sample and diluent from said first reaction tubes, to a position for discharging sample and diluent into said second reaction tubes, and to a position adjacent said cleaning means for being cleaned thereby.

6. An automatic analytical apparatus comprising:

a plurality of cups for containing samples to be analyzed;

a sample cassette for holding said plurality of cups;

a transport turret rotatable about a first axis and having disposed thereon a first plurality of reaction tubes;

means for moving said transport turret to move said first plurality of reaction tubes to any of a number of discrete stations along a closed path;

diluent pipetting means operatively associated with said transport turret for pipetting measured amounts of diluent into said first reaction tubes containing said samples;

a measuring turret rotatable about a second axis and having a second plurality of reaction tubes disposed substantially at a circumference thereof;

means for moving said measuring turret to move said second plurality of reaction tubes to any of a number of discrete stations along a closed path;

a reagent turret coaxial with said measuring turret, being rotatable with respect to said measuring turret about said second axis, there being a plurality of reagent containers mounted thereon and a plurality of reagent pipetting means also mounted thereon and respectively associated with said plurality of reagent containers for pipetting measured amounts of reagent into said second reaction tubes containing said samples and diluent;

means for moving said reagent turret with respect to said measuring turret so as to selectively position any desired one of said reagent containers and the associated reagent pipetting means at a desired one of said discrete stations;

a holding means arranged adjacent said measuring turret at one of said discrete stations thereof, said holding means comprising means for engaging a pipette of one of said reagent pipetting means and moving the engaged pipette between the reagent container associated with the pipette and a reaction tube;

first pipette sample transfer means for pipetting samples contained din said cups into said first reaction tubes;

second pipette sample transfer means disposed between said measuring and transport turrets for taking up measured amounts of said sample and diluent from said first reaction tubes and for discharging said measured amounts into said second reaction tubes, said second pipette sample transfer means comprising a pipette holder turret rotatable through predetermined indexing angles, a plurality of pipettes disposed on said pipette holder turret, driving means for intermittently indexing said pipette holder turret, and pumping means for effecting said taking up and discharging of said measured amount of sample and diluent;

optical measuring means operatively associated with said measuring turret for making an absorptiometry measurement of said samples, diluent and reagent while contained in said second reaction tubes, by use of a light beam, at a given one of said stations of said measuring turret; and control means for respectively operating during sequential time intervals said first and second pipette sample transfer means, said means for moving said transport turret, said means for moving said measuring turret, and said means for moving said reagent turret, said control means being effective during a time interval to cause, substantially simultaneously;

said motion of said transport turret, said indexing of said second pipette sample transfer means, said rotation of said measuring turret, and said motion of said reagent turret to bring any of said reagent containers to any desired station of said measuring turret.

* * * * *